US00PP26581P3

(12) United States Plant Patent
Werner

(10) Patent No.: US PP26,581 P3
(45) Date of Patent: Apr. 5, 2016

(54) ***BUDDLEJA* PLANT NAMED 'BLUE CHIP JR'**

(50) Latin Name: ***Buddleja* hybrid**
Varietal Denomination: Blue Chip Jr

(71) Applicant: North Carolina State University, Raleigh, NC (US)

(72) Inventor: Dennis James Werner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 132 days.

(21) Appl. No.: 13/999,798

(22) Filed: Mar. 21, 2014

(65) Prior Publication Data

US 2015/0052650 P1 Feb. 19, 2015

(30) Foreign Application Priority Data

Aug. 19, 2013 (CA) ..... PBR 13-8095

(51) Int. Cl.
*A01H 5/02* (2006.01)

(52) U.S. Cl.
USPC ..... Plt./242
CPC ..... *A01H 5/02* (2013.01)

(58) Field of Classification Search
USPC ..... Plt./242
See application file for complete search history.

(56) References Cited

PUBLICATIONS

Flowering Shrubs, Spring Meadow Nursery, Inc. Starter Plants Catalog and Shrub Reference 2013-2014; Aug. 25, 2013, pp. 11.

*Primary Examiner* — June Hwu
(74) *Attorney, Agent, or Firm* — Myers Bigel & Sibley, P.A.

(57) ABSTRACT

*Buddleja* 'Blue Chip Jr' is a new and distinct variety of butterfly bush that has the following unique combination of desirable features that are outstanding in a new variety. 'Blue Chip Jr' has low vigor resulting in very dwarf stature. 'Blue Chip Jr' is asexually propagated using softwood or semi-hardwood cuttings. 'Blue Chip Jr' demonstrates a dense, spreading growth habit. 'Blue Chip Jr' is lacking male flower parts (anthers), resulting in male (pollen) sterility. 'Blue Chip Jr' produces female structures that are essentially sterile, resulting in lack of seed formation. 'Blue Chip Jr' has purple-violet flower color.

4 Drawing Sheets

Latin name of the genus and species: Genus: *Buddleja*. Species: hybrid.

Variety denomination: The inventive cultivar of *Buddleja* disclosed herein has been given the variety denomination 'Blue Chip Jr'.

RELATED APPLICATION INFORMATION

This application claims priority under 35 U.S. §119(a) to Canadian Plant Breeder's Rights Application No. 13-8095, filed Aug. 19, 2013; the disclosure of which is incorporated herein by reference in its entirety.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventor in Raleigh, N.C., United States. One of the objectives of the breeding program was to develop a very dwarf, spreading *Buddleja* with purple-violet flowers. 'Blue Chip Jr' was selected at a research station in Jackson Springs, N.C. in 2009 from a population of about 100 seedling progeny derived from a hand pollinated cross of 'Blue Chip' (tested as NC2004-9)×NC2006-18 (advanced test selection) made in summer 2008 in Raleigh, N.C. 'Blue Chip' was the female (seed) parent, and NC2006-18 was the male (pollen) parent in the aforementioned hybridization. 'Blue Chip' is a complex hybrid containing 3 different species and one botanical variety of *Buddleja* (*B. davidii, B. davidii* var. *nanhoensis, B. lindleyana,* and *B. globosa*). NC2006-18, the other parent of 'Blue Chip Jr', is a hybrid of NC2003-13×'Miss Molly'. 'Miss Molly' was derived from hybridization of 'Miss Ruby'×'Attraction'. NC2003-13 is a hybrid of NC2001-3× 'Ellen's Blue'. 'Miss Ruby' was derived from hybridization of 'White Ball'×'Attraction'. NC2001-3 was derived from open pollination of NC2000-1. 'White Ball' is a complex hybrid, presumably containing *B. davidii* and *B. fallowiana.* 'Attraction' was derived as an open-pollinated seedling of 'Honeycomb', which is a hybrid of *B. globosa*×*B. davidii*. NC2000-1 is a hybrid of 'Nanho Purple'×*Buddleja lindleyana*. 'Nanho Purple' is a variety derived from *Buddleja davidii* var. *nanhoensis*. All of the hybridizations described above, with the exception of the development of 'White Ball' and 'Attraction', were accomplished in the inventor's research program. The complete pedigree of 'Blue Chip Jr' is shown in FIG. 4. Of all the parents used in the development of 'Blue Chip Jr', the varieties 'Blue Chip' (U.S. Plant Pat. No. 19,991), 'Miss Molly' (U.S. Plant Pat. No. 23,425), 'Miss Ruby' (U.S. Plant Pat. No. 19,950), 'Attraction' (not patented), 'White Ball' (not patented), 'Ellen's Blue' (not patented), 'Nanho Purple' (not patented), and 'Honeycomb' (not patented), and the species *Buddleja lindleyana* are available in commerce.

The seeds resulting from the 2008 controlled hybridization process were harvested in fall of 2008 and germinated in a greenhouse in Raleigh, N.C. in the winter of 2009. The resulting 100 seedlings (approximate) were planted in field trials in spring of 2009 at a research station in Jackson Springs, N.C. These plants flowered in summer 2009, and one plant, designated NC2009-3, was selected on Aug. 14, 2009 for its very dwarf plant size, spreading habit, attractive purple-violet (RHS N82A) colored flowers, obovate leaves, flowers lacking anthers (male sterile), and lack of seed set (female sterile). This original plant demonstrated characteristics identical to those subsequently expressed on other plants when propagated from stem cuttings. This single plant is the subject of the present invention *Buddleja* 'Blue Chip Jr'.

The inventor conducted the first asexual propagation of 'Blue Chip Jr' in fall 2009 in Raleigh, N.C., and 'Blue Chip Jr' has subsequently been propagated in the same location in years 2010 through 2013. In all cases, the original plant selection was propagated asexually by softwood to semi-hardwood stem cuttings. Such cuttings root readily under mist in about 14 to 21 days, and resume normal growth. Six plants derived from stem cuttings of the variety were established in experimental greenhouse trials in Raleigh, N.C. in fall, 2009 and in 2010. Subsequently, ten plants derived from stem cuttings were established in a field trial in Jackson Springs, N.C. in 2013. Through successive asexual propagations, the characteristics of the original plant have been maintained. Thus, plants derived from stem cuttings exhibit characteristics identical to those of the original plant, and no aberrant phenotypes have appeared.

Test plantings and performance evaluation over five years at a research station in Jackson Springs, N.C. and a greenhouse in Raleigh, N.C. demonstrate this variety to be relatively consistent in its characteristics even under the different growing conditions associated with yearly climatic variation.

Plants of the new variety are very dwarf after establishment in the field, being less vigorous and more dwarf than most cultivars of butterfly bush in commerce. Young plants have averaged about 45 cm of height growth per year. Plants are spreading in growth habit. Flowering occurs in the first year of growth on newly formed wood. The inflorescence is a panicle, and shows a purple-violet flower (RHS N82A) color. Flowering usually begins in late May to early June in Jackson Springs, N.C., and continues throughout the growing season until the first freeze event in October or November. An individual inflorescence flowers for about 7-10 days, depending on temperature, but new flowers are made during the entire growing season. Flowers are essentially female sterile, and the new cultivar has set no seed to date in greenhouse or field trials, even under conditions of intentional controlled pollination, an asset in landscape plantings.

The distinguishing traits of 'Blue Chip Jr' are very dwarf plant size, dense spreading growth habit, green obovate leaves (RHS 137C), attractive purple-violet flower color, lack of anthers (male sterility), and female structures that are essentially sterile. "Essentially sterile" is used because applicant does not preclude the possibility that seed set may be observed on rare occasions. The cultural requirements for 'Blue Chip Jr' are well-drained soil, full to part-sun exposure, and moderate moisture. 'Blue Chip Jr' exhibits no serious pest or disease problems known to the inventors, except for occasional spider mite infestation during periods of hot, dry weather.

SUMMARY OF THE INVENTION

'Blue Chip Jr' is a new and distinct variety of butterfly bush that has the following unique combination of desirable features outstanding in a new variety. In combination these traits set 'Blue Chip Jr' apart from all other existing varieties of butterfly bush known to the inventors.

1. 'Blue Chip Jr' has low vigor resulting in very dwarf stature.
2. 'Blue Chip Jr' is asexually propagated using softwood or semi-hardwood cuttings.
3. 'Blue Chip Jr' demonstrates a dense, spreading growth habit.
4. 'Blue Chip Jr' exhibits absence of anthers (male sterility).
5. 'Blue Chip Jr' has female structures that are essentially sterile (female sterility).
6. 'Blue Chip Jr' has purple-violet flower (RHS N82A) color.
7. 'Blue Chip Jr' has obovate leaf shape.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'Blue Chip Jr'. Photographs were taken from one-year-old plants growing in Jackson Springs, N.C.

DETAILED BOTANICAL DESCRIPTION OF THE VARIETY

The following is a detailed description of the botanical and ornamental characteristics of the subject butterfly bush 'Blue Chip Jr'. Color data are based on *The Royal Horticultural Society Colour Chart*, The Royal Horticultural Society, London, 2007 edition. Where dimensions, sizes, colors and other characteristics are given, it is to be understood that such characteristics are approximations of averages set forth as accurately as practicable.

The descriptions reported herein are from one-year-old specimens grown in field research trials in Jackson Springs, N.C.

Genus: *Buddleja.*

Species: Complex hybrid, including *davidii, fallowiana, globosa*, and *lindleyana.*

Denomination: 'Blue Chip Jr'.

Commercial classification: Shrub, deciduous.

Common name: Butterfly bush.

Type: Ornamental.

Uses: Patio container plant, herbaceous perennial border, or shrub border for residential and commercial landscapes.

Cultural requirements: Full sun exposure, well-drained soil, and moderate moisture.

Figure 1:
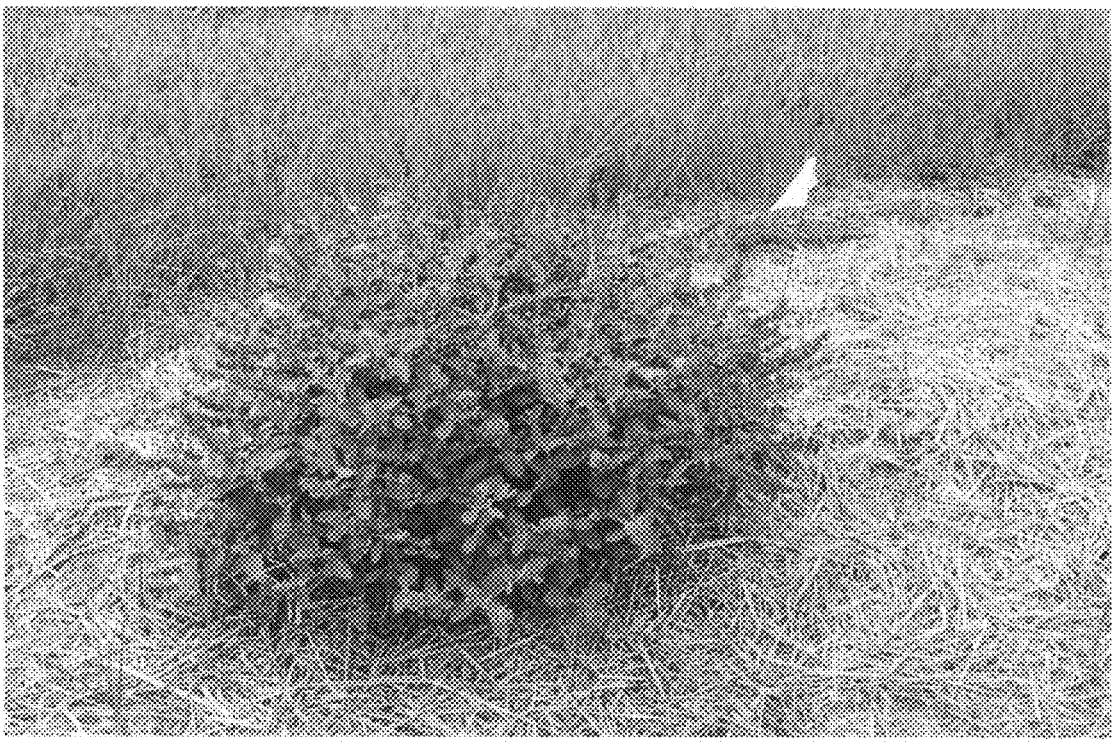
FIG. 1 shows a typical plant of 'Blue Chip Jr', showing the dwarf stature, spreading growth habit, dense foliage, and purple-violet (RHS N82A) flowers.
Figure 2:
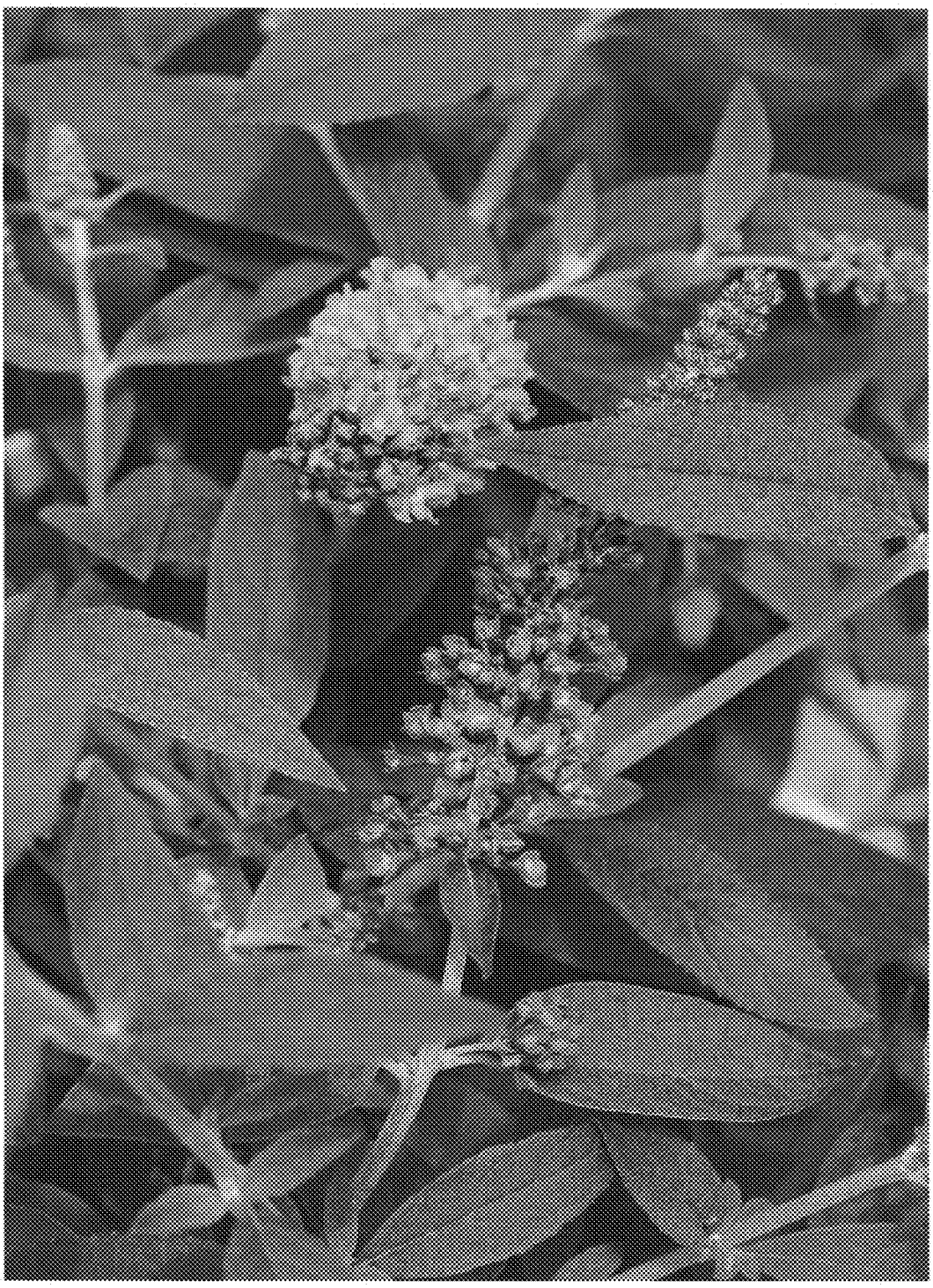
FIG. 2 shows the entire inflorescence of 'Blue Chip Jr'.
Figure 3:
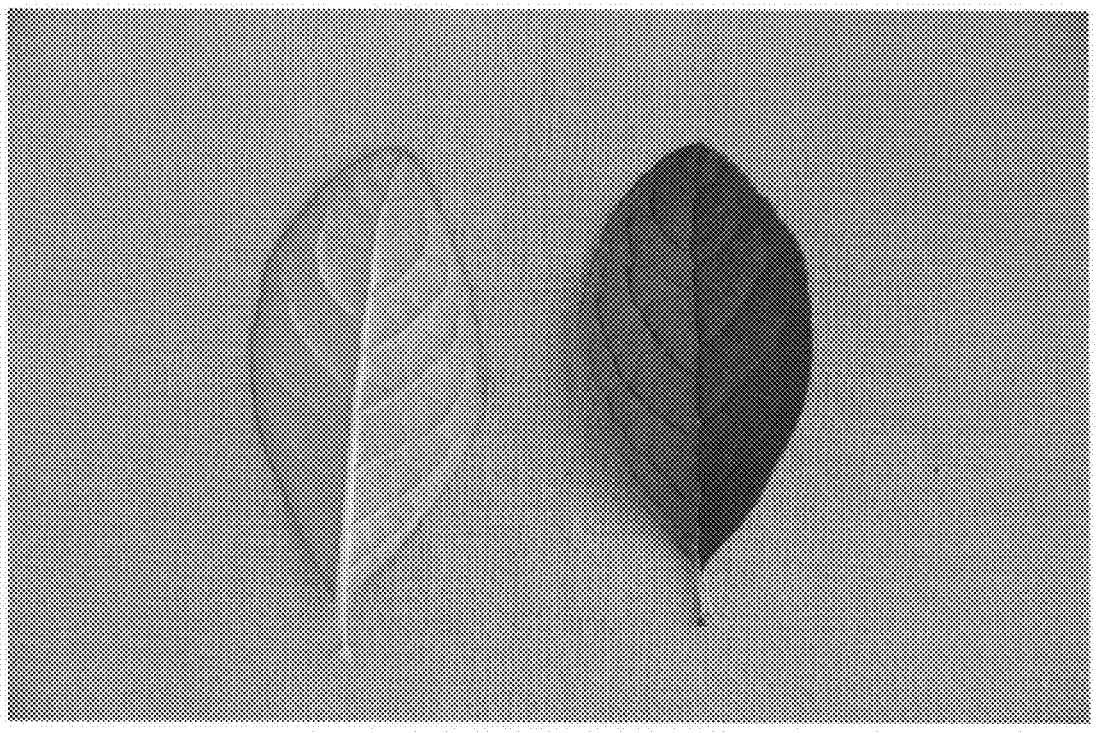
FIG. 3 shows the typical coloration and form of leaves of 'Blue Chip Jr'. This figure shows the lower (left) and upper (right) leaf surface.
Figure 4:
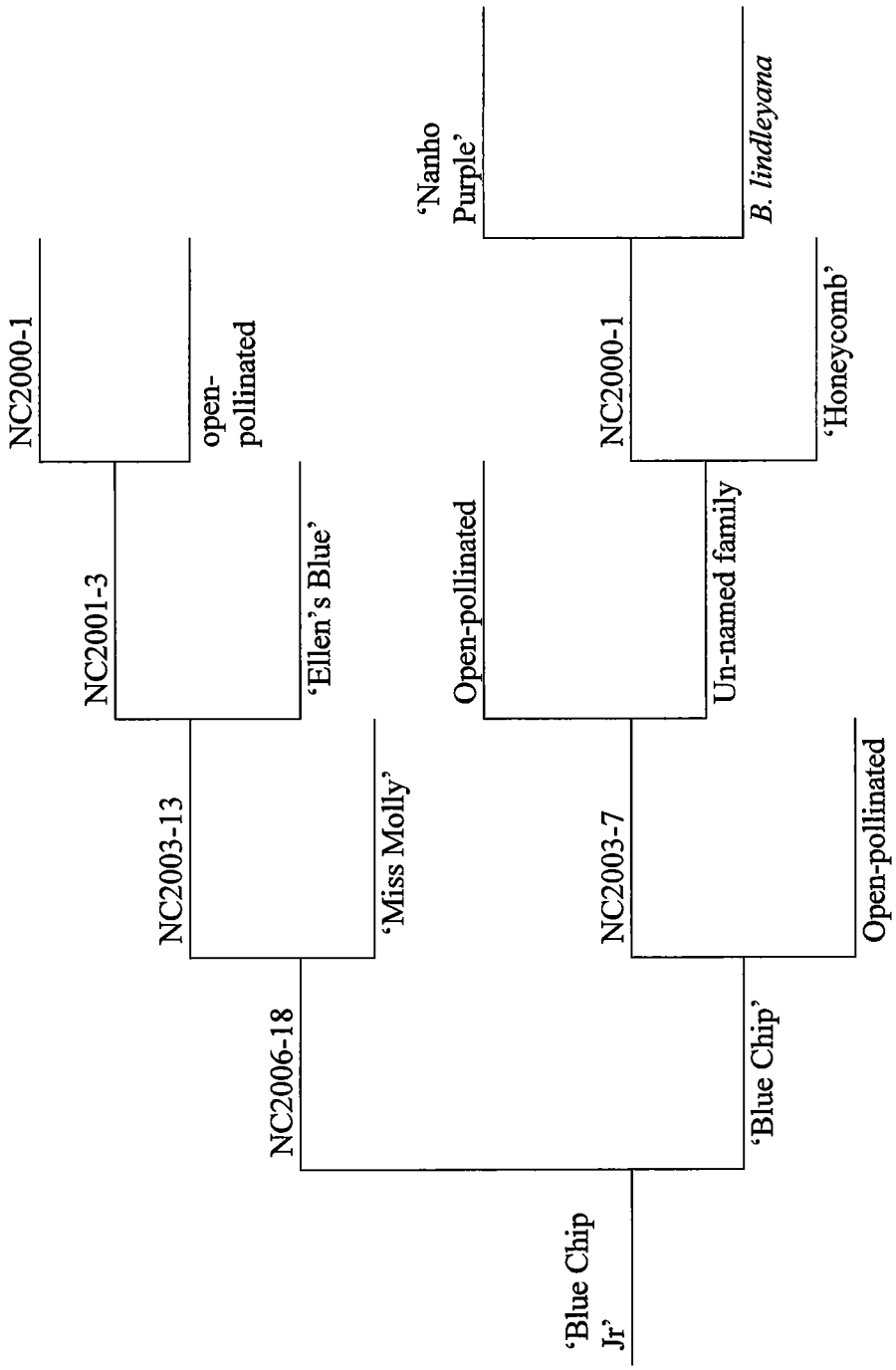
FIG. 4 shows the complete pedigree of 'Blue Chip Jr'.

Parentage: 'Blue Chip Jr' is a sixth-generation hybrid that resulted from the most recent cross pollination of 'Blue Chip'×NC2006-18. See FIG. 4 for the entire pedigree.

Plant description:

*Blooming period*.—June through October.

*Blooming habit*.—Paniculate.

*Vigor*.—Low vigor.

*Plant habit*.—Dwarf, spreading habit.

*Height and spread*.—0.45 m (height) and 0.96 m (width) on one-year-old unpruned plants.

*Hardiness*.—To date, hardy to minus 14 degrees Centigrade (7 degrees Fahrenheit). Not tested below this temperature. Anticipated adapted to USDA hardiness zones 5-9.

*Propagation*.—Softwood to semi-hardwood cuttings under intermittent mist. Roots typically form in 2-3 weeks.

*Root system*.—Fibrous, spreading.

*Seasonal interest*.—Purple-violet flowers in spring, summer, and fall on a very dwarf shrub with spreading growth habit.

*Disease and pest susceptibility and resistance*.—No particular susceptibility or resistance, except occasionally susceptible to spider mites under very hot and dry conditions.

*Special growing requirements*.—Moderate yearly pruning in late winter or early spring prior to bud break is recommended to encourage more profuse flowering.

Stems:

*Shape*.—Stem cross section is quadrangular.

*Length*.—Average 46 cm in one year of growth.

*Color*.—Yellow-green (RHS 145C) on recently formed shoots.

*Diameter*.—2.6 mm at base of new growth.

*Stem surface*.—Slight pubescence.

*Pubescence*.—Sparse.

*Internode length*.—4.8 cm in the middle of new growth.

Foliage:

*Type*.—Deciduous.

*Leaf arrangement*.—Opposite, decussate.

*Leaf division*.—Simple.

*Leaf shape*.—Obovate.

*Leaf base*.—Attenuate.

*Leaf apex*.—Sub-obtuse.

*Leaf venation*.—Pinnate.

*Leaf surface* (*abaxial*).—Glaucous.

*Leaf margin*.—Entire near leaf base, transitioning to slightly serrulate toward leaf apex.

*Leaf attachment*.—Petiolate.

*Petiole dimensions*.—6.2 mm length. 1.6 mm width.

*Petiole shape*.—Sulcate and pubescent.

*Petiole color*.—Yellow-green (RHS 146C).

*Leaf color*.—Adaxial side=green (RHS 137C). Abaxial side=grayed-green (RHS 191A).

*Leaf midrib color*.—Abaxial side=greyed-green (RHS 194C).

*Leaf length*.—Average length=5.5 cm.

*Leaf width*.—Average width=2.6 cm.

*Foliar fragrance*.—None detectable.

Flowers:

*Inflorescence*.—Dense panicle, terminal and axillary.

*Inflorescence shape*.—Cylindrical.

*Flower shape*.—Salverform.

*Petals*.—4 in number.

*Fused or unfused*.—Fused at base.

*Petal margin*.—Entire.

*Petal apex*.—Rounded lobes, serrulate.

*Petal base*.—Truncate.

*Petal surfaces*.—Lacking pubescence.

*Petal shape*.—Rotund.

*Petal dimensions*.—9.2 mm total length. 5.6 mm width at apex. 1.5 mm width at base.

*Petal color excluding margin color*.—Adaxial and abaxial surface (open flower) RHS N82A (purple-violet group).

*Petal margin color*.—RHS 83B (violet group). Closed flower prior to opening=Violet (RHS 83A).

*Corolla tube color*.—Outside of corolla=Purple-violet (RHS N82A).

*Corolla throat color*.—Inside of corolla=Yellow-orange (RHS 22A).

*Corolla tube surfaces* (*inner and outer surfaces*).—Pubescence lacking.

*Corolla tube shape*.—Tubular.

*Corolla tube length*.—5 mm.

*Corolla tube width*.—1 mm.

*Corolla lobe arrangement*.—Touching to slightly overlapping.

*Corolla lobe attitude*.—Semi-erect.

*Corolla eye*.—RHS N155C (white group).

*Color of peduncle*.—Green (RHS 142B).

*Peduncle surface*.—Glaucous.

*Peduncle length*.—10 cm.

*Peduncle shape*.—Flattened oval in cross section.

*Pedicel dimensions*.—2.1 mm in length and less than 1 mm in diameter.

*Pedicel color*.—Green (RHS 142B).

*Pedicel shape*.—Flattened oval in cross section.

*Pedicel surface*.—Glaucous.

*Flowers persistent or self-cleaning*.—Flowers are persistent.

*Lastingness of the overall inflorescence*.—7-10 days.

*Lastingness of an individual flower*.—3-5 days.

*Dimensions of inflorescence*.—10 cm length. 1.3 cm width at base, tapering to 0.5 cm at tip.

*Quantity of flowers*.—76.8 flowers per panicle (average number of panicles sampled was 5).

*Bud apex*.—Rounded lobes, serrulate.

*Bud surface*.—Glaucous. Lacking pubescence.

*Bud shape*.—Elongated, linear balloon.

*Calyx shape*.—Tubular.

*Calyx dimensions*.—1 mm in width and 3.6 mm in length.

*Sepals*.—Four in number.

*Sepal shape*.—Lanceolate.

*Sepal apex*.—Acute.

*Sepal margin*.—Entire.

*Sepal surface*.—Glabrous.

*Sepal color*.—Greyed-green (RHS 194C).

*Flower fragrance*.—Distinct sweet fragrance.

Reproductive organs:

*Stamens*.—Absent.

*Anther shape*.—Absent.

*Filament size*.—Absent.

*Pollen amount*.—Absent.

*Pistil*.—One in number.

*Pistil dimensions.*—3 mm in length, and less than 1 mm in diameter.

*Stigma color.*—Yellow-green (RHS 144B).

*Style color.*—Yellow-green (RHS 144D).

*Ovary.*—Present.

*Ovary position.*—Superior.

*Ovary shape.*—Oval.

*Fertility.*—Essentially male (pollen) and female (seed) sterile.

Fruit:

*Type.*—Absent. Essentially female sterile.

*Dimensions.*—Absent.

*Color.*—Absent.

Comparison with known cultivars. The closest comparisons known to the inventor are the varieties 'Blue Chip' (U.S. Plant Pat. No. 19,991), and 'White Ball' (non-patented). Plants and flowers of this new variety differ from 'Blue Chip'. In direct comparisons of 'Blue Chip Jr' and 'Blue Chip' in the inventor's experimental trials, plants of 'Blue Chip Jr' are more compact, and have obovate leaves compared to the more lanceolate leaves of 'Blue Chip'. 'Blue Chip Jr' has female structures that are essentially sterile, compared to the low female fertility of 'Blue Chip'. 'Blue Chip Jr' also possesses longer panicles (inflorescences) than 'Blue Chip'. In replicated trials of 10 plants of both varieties, one-year-old unpruned plants of 'Blue Chip Jr' attained a height and spread of 45 and 96 cm, respectively (height/width ratio=0.47), after one year of growth. Plants of 'Blue Chip' attained a height and spread of 62.0 cm and 143 cm (height/width ratio=0.44), respectively. 'Blue Chip Jr' is distinctly different from 'White Ball'. In direct comparisons of 'Blue Chip Jr' and 'White Ball' in the inventor's experimental trials, plants of 'Blue Chip Jr' are consistently more spreading as compared to the globose architecture of 'White Ball'. 'Blue Chip Jr' is shorter in height and has purple-violet flowers (RHS N82A) as compared to the white flowers of 'White Ball'. No comparison of 'Blue Chip Jr' with its paternal (pollen) parent NC2006-18 can be made as this advanced selection is no longer extant in the breeding program.

Herbarium Voucher:

A voucher of 'Blue Chip Jr' will be deposited into the Herbarium of North Carolina State University (NCSU) in Raleigh, N.C., USA upon patenting.

That which is claimed is:

1. A new and distinct variety of butterfly bush (*Buddleja*) named 'Blue Chip Jr' substantially as illustrated and described herein, characterized by its dwarf stature, dense and spreading growth habit, obovate leaf shape, purple-violet flower color, lack of male flower parts (anthers) resulting in male sterility, and female structures that are essentially sterile, resulting in no seed formation.

* * * * *